United States Patent [19]
Auth

[11] Patent Number: 4,646,736
[45] Date of Patent: Mar. 3, 1987

[54] TRANSLUMINAL THROMBECTOMY APPARATUS

[75] Inventor: David C. Auth, Bellevue, Wash.

[73] Assignee: E. R. Squibb & Sons, Inc., Princeton, N.J.

[21] Appl. No.: 889,600

[22] Filed: Jul. 25, 1986

Related U.S. Application Data

[63] Continuation of Ser. No. 649,089, Sep. 10, 1984, abandoned.

[51] Int. Cl.⁴ ............................................. A61B 17/00
[52] U.S. Cl. ................................................. 128/303 R
[58] Field of Search ............... 128/305, 305.1, 303 R, 128/304, 751, 752; 604/22

[56] References Cited

U.S. PATENT DOCUMENTS

| | | | |
|---|---|---|---|
| 3,614,953 | 10/1971 | Moss | 128/305.1 |
| 3,935,857 | 2/1976 | Co | 604/281 |
| 3,937,222 | 2/1976 | Banko | 128/305 |
| 4,273,128 | 6/1981 | Lary | 128/305 |

FOREIGN PATENT DOCUMENTS

| | | | |
|---|---|---|---|
| 0086048 | 8/1983 | European Pat. Off. | 128/305 |
| 442795 | 9/1974 | U.S.S.R. | 128/305.1 |

Primary Examiner—Michael H. Thaler
Attorney, Agent, or Firm—Lawrence S. Levinson; Sanford J. Asman

[57] ABSTRACT

The invention is an apparatus for breaking up a thrombus by introducing a rotating drive shaft into the thrombus whereby the fibrin of the thrombus will be withdrawn from the thrombus onto the rotating drive shaft, thereby breaking up the network of the thrombus which prevents blood flow. The apparatus includes a drive shaft housing which can be used to withdraw fluid from the area of the thrombus or to introduce medicines, such as streptokinase which will further break up the thrombus or other chemicals such as contrast agents for visualizing the vascular anatomy.

18 Claims, 5 Drawing Figures

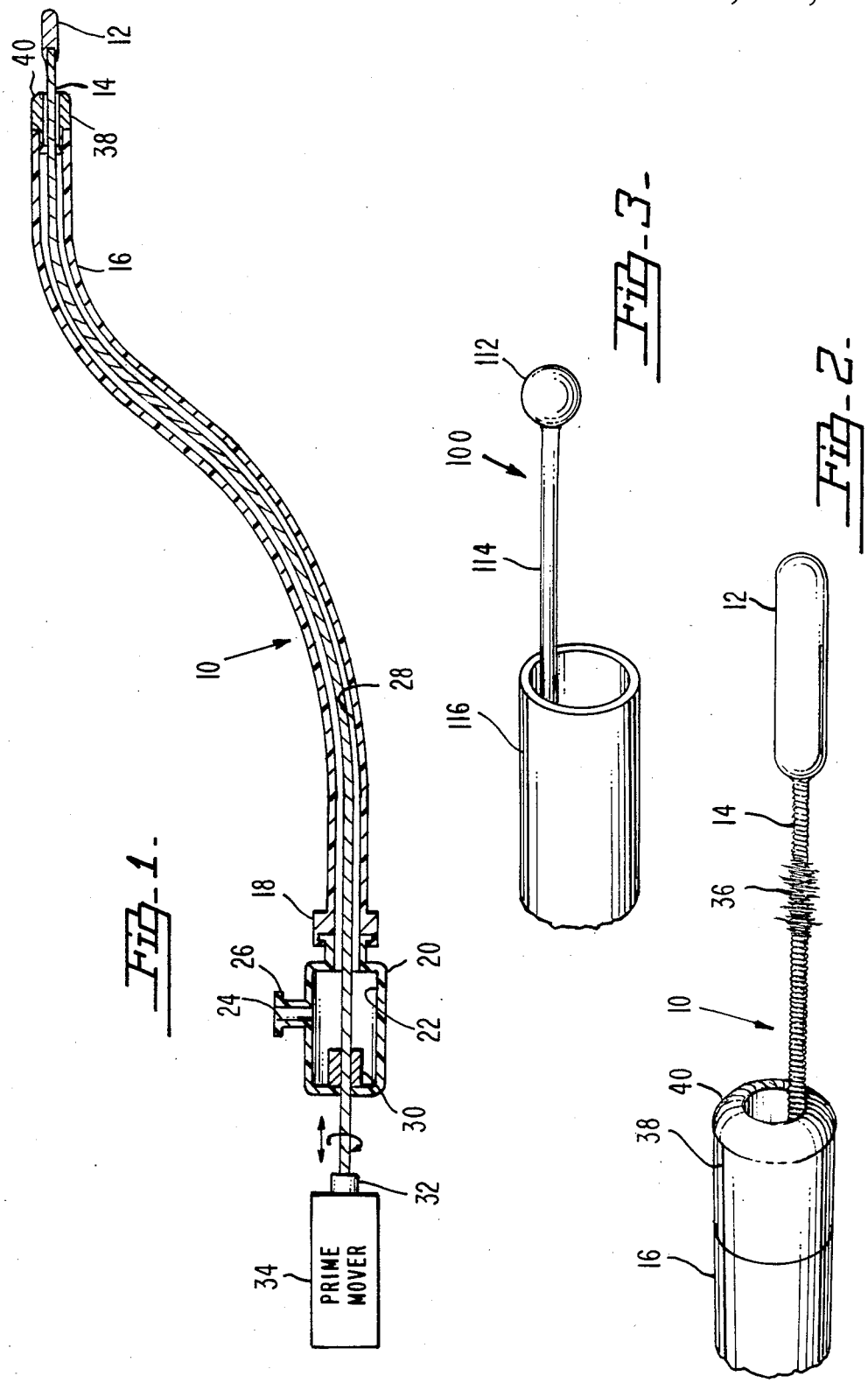

TRANSLUMINAL THROMBECTOMY APPARATUS

This is a continuation of co-pending application Ser. No. 649,089 filed on Sept. 10, 1984, now abandoned.

BACKGROUND OF THE INVENTION

The present invention relates to a device used to break up blood clots or thrombi which form within arteries. In particular, the device is particularly well adapted to break up such clots or thrombi which may form within a coronary artery.

Approximately 1.2 million Americans suffer heart attacks each year. A large percentage of the heart attacks are caused by blood clots or thrombi which form within the coronary arteries. A thrombus is nature's way of stemming the loss of blood from its pipeline system by corking off an opening into the vascular tree. The biochemical process which results in thrombus formation is not fully understood. However, in simple terms, injury to the vascular wall releases chemicals which lead to conversion of soluble circulating fibrinogen molecules into a polymeric structure of fibrin. The fibrin structure is insoluble and arranges itself into a three dimensional network of meshed strands which entraps red blood cells. The individual strands are approximately 0.2 microns in diameter and the mesh size is approximately 1 micron. Accordingly, five micron red blood cells are easily trapped within the three dimensional "net".

When a thrombus forms, it effectively stops the flow of blood through the zone of formation. If the thrombus extends across the interior diameter of an artery, it cuts off the flow of blood through the artery. If one of the coronary arteries is 100% thrombosed, the flow of blood is stopped in that artery resulting in a shortage of oxygen carrying red blood cells to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Coronary artery bypass graft (CABG) surgery is a surgical method for bypassing coronary arteries which, because of narrowing or obstruction, are unable to supply adequate oxygen to heart muscle. In recent years, direct administration of chemical lysing agents into the coronary arteries has shown to be of some benefit to patients who have thrombosed coronary arteries. In this procedure, a catheter is placed immediately in front of the blockage and a drip of streptokinase is positioned to be directed at the upstream side of the thrombus. Streptokinase is an enzyme which is able in time to dissolve the fibrin molecule. This procedure can take several hours and is not always successful in breaking up the thrombus. Furthermore, it can lead to downstream thrombus fragments (emboli) which can lead to blockage of smaller diameter branches. It would be useful to have a device and method which would permit essentially instantaneous removal of the blocking thrombus.

SUMMARY OF THE INVENTION

The present invention is a transluminal thrombectomy apparatus. It comprises a flexible drive shaft having a tip affixed thereto. The tip has a diameter which is greater than the diameter of the drive shaft. The tip is an elongated cylinder with rounded ends. The apparatus further comprises a flexible, cylindrical shaft housing having an inside diameter which is greater than the outside diameter of the tip. The shaft housing extends along and surrounds the drive shaft. The device includes connecting means for sealably connecting the end of the shaft housing which is remote from the tip to an apparatus capable of providing a fluid path through the drive shaft housing to the end of the drive shaft housing at which the tip is located. In addition, the device includes drive shaft connecting means at the end of the drive shaft which extends through the shaft housing connecting means for connecting the drive shaft to a rotating prime mover.

BRIEF DESCRIPTION OF THE DRAWING

In the Drawing:

FIG. 1 is a cross-sectional pictorial view showing the present invention set up for use;

FIG. 2 is a side view of a first embodiment of the invention;

FIG. 3 is a side view of a second embodiment of the invention;

DETAILED DESCRIPTION OF THE PREFERRED EMBODIMENT

Figure 4:
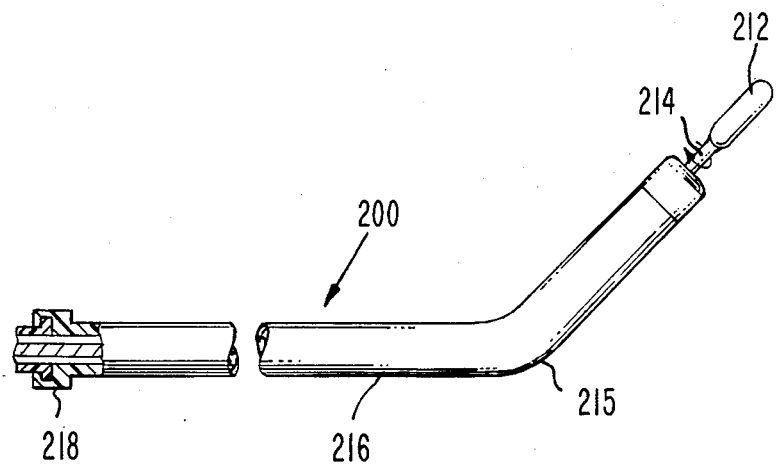
FIG. 4 is a side view of a steerable embodiment of the invention.

FIG. 1 illustrates the transluminal thombectomy apparatus 10 of the present invention. The device 10 preferably includes an elongated, cylindrical atraumatic tip 12 having rounded ends which is rotated by a transluminal drive shaft 14. The drive shaft 14 is contained within a flexible shaft housing 16 which is typically made of a plastic material. The inside diameter of the shaft housing 16 is preferably selected to be greater than the diameter of the tip 12 in order that the tip 12 can be withdrawn into the shaft housing 16. At the end of the shaft housing 16 remote from the tip 12 there is preferably a shaft housing connector 18 which may be used to quickly connect the shaft housing 16 to a drive shaft bearing block and shaft seal 20. The shaft housing connector 18 permits rotation of the shaft housing 16 for reasons which will be explained.

The drive shaft bearing block and shaft seal 20 is a body which has a central cavity 22 and a port 24 connected thereto. The port 24 also includes a quick connect fitting 26 in order that a fluid path exists from the port 24 through the central cavity 22 and through the interior lumen 28 of the shaft housing 16. This fluid connection can be used either to withdraw fluid through the shaft housing 16 or to dispense drugs, such as streptokinase, through the shaft housing 16. A fluid seal 30 which allows axial movement of the drive shaft 14 is at one end of the drive shaft bearing block and shaft seal 20. The end 32 of the drive shaft 14 remote from the tip 12 is connected to a rotary prime mover 34.

In operation, the rotating tip 12 is pushed into a thrombus. Because the tip 12 is rotated, it is able to cause fibrin 36 to be wound around its narrow shaft 14 (See FIG. 2). This happens because of friction between the surface of the rotating drive shaft 14 and because of a localized "whirlpool" in any free liquid surrounding the tip 12 and the shaft 14. As the fibers 36 follow about the rotating tip 12, their tension increases, further tightening their grip on the drive shaft 14 and eventually stripping away an interior volume of the fibrin network. Red blood cells which were entrapped can be released back into the circulatory system without emboli-producing large fragments, since the insoluble material is retained on the drive shaft 14 for later extraction from the body.

As shown in FIG. 2, the fibrin 36 winds around the drive shaft 14 when the rotating tip 12 and drive shaft 14 pass through a clot. Since the fibrin 36 winds very tightly around the drive shaft 14, and since the fibrin 36 constitutes only about 4% of the volume of the thrombus, it is possible to strip the clot's framework and thereby eliminate a large volume of the clot before the tip 12 of the thrombectomy apparatus 10 needs to be withdrawn from the patient for cleaning or replacement. In most cases, the entire thrombectomy can be performed without using up the fibrin storage capacity of the thrombectomy tip 12.

As shown in FIG. 1, the tip 12 is comprised of a generally sausage shaped radiopaque piece affixed to a cylindrical metal drive shaft 14. The rounded edges of the front and rear of the tip 12 reduce the probability of inadverent perforation of vessel walls and the thin drive shaft 14 provides torque transmission as well as an area for coiling and storing the fibrin. In the preferred embodiment of the invention, the tip 12 has a diameter of about 25 mils and a length of about 80 mils, and it is mounted on a 5 mil stainless steel drive shaft 14. As will be understood by those skilled in the art, it could be advantageous to have tips with diameters as small as 10 mils to negotiate very tiny arteries and narrowed segments. In such cases, the drive shaft 14 would be proportionately smaller or compliant to the tip 12 in order to avoid ram puncture of an artery. While the tip 12 of the preferred embodiment 10 is an oblong cylinder with rounded ends, a spheroidal tip 112, as shown in FIG. 3, could also be used with some loss of radiovisualization. In the preferred embodiment 10 of the invention, the tip 12 is made of a radiopaque material, such as platinum filled plastic, and it is attached to the drive shaft 14 by gluing or welding or soldering. When viewed angiographically, the elongated sausage shape of the tip 12 is quickly visualized with its axis clearly defined. Having an elongated geometry facilitates localization on raster scanned video displays.

In order to provide angiographic surveillance of the end of the shaft housing 16, a special end-cap 38 is preferably affixed thereto. The end-cap 38 is also made to be radiopaque by fabricating it from solid platinum or a platinum alloy, or by molding, preferably from a radiopaque-filled plastic. In the preferred embodiment, the end-cap 38 is machined from platinum and glued to the shaft housing 16. The end-cap 38 has been visualized under an angiography machine along with the platinum sausage shaped tip 12, and there is an extremely clear and easily read image of the respective components 12, 38. The end-cap 38 also serves as a bearing surface for the drive shaft 14 and greatly improves passage of the device 10 through a vessel since its shoulders 40 are rounded (It is difficult to provide good sliding characteristics with the plastic shaft housing 16, because the wall thickness is too small to adequately round shoulders on it. Increasing the wall thickness of the shaft housing 16 reduces the lumen available for injection of chemicals such as contrast agents).

Referring to FIG. 2, the drive shaft 14 of the embodiment 10 is comprised of a 3 mil gold wire which is helically wound around a 4 mil stainless steel arbor (not shown). The use of gold is particularly appropriate, since it is highly radiopaque and exhibits high fatigue resistance. Since flexibility is improved by using a helical wire lay-up, it may be advantageous in reducing perforation of the vessel wall by, in effect, having a "softer" tip 12 for a given diameter drive shaft 14. Deliberate roughening of a solid drive shaft, such as the drive shaft 114 shown in the embodiment 100 of FIG. 3, or adjusting the spacing of the helical lay-up on the composite drive shaft 14 might be desirable in some clinical applications where fibrous material is more resistant to coiling and capture.

As described above, in the embodiment 10, the drive shaft 14 is housed in a tubular shaft housing 16 which can be used as a conduit for infusion of fluids, including those that aid thrombolysis. It can also be used to monitor pressure or suck the thrombus or clot onto the rotating tip 12 and up the shaft housing 16.

In order to use the device 10, the drive shaft 14 and tip 12 are rotated by a prime mover 34 at a speed which is preferably in the range 500–6000 rpm for coiling of fibrin. Higher speeds may be used, but they are unnecessary. If the speed is reduced too much, the advantage of "orthogonal velocity vector displacement" of longitudinal friction is lost. If the tip 12 is advanced without rotation into the thrombus, it will, if advanced very slowly, have a tendency to jerk forward due to frictional force on the drive shaft/housing and frictional forces on the tip/thrombus interface. Without rotation and with steady longitudinal advance, the dynamic coefficient of friction will govern the force required through the catheter and into the thrombus.

The addition of rotation to the shaft 14 and tip 12 results in tipping the friction vector away from the longitudinal direction toward the circumferential direction. Since the magnitude of the dynamic coefficient of friction is normally quite constant independent of velocity, the magnitude of the total friction vector is essentially constant. With a constant magnitude of friction, the more rotational speed imparted to the drive shaft 14 and tip 12, the more the friction vector is tipped away from the longitudinal direction. The result is a reduction of longitudinal force required to slide in the longitudinal direction. This diminishes the force required to push the catheter along the shaft housing 16 and the force required to penetrate a thrombus. With less force required to advance the tip 12, less distention and bowing of the drive shaft 14 and shaft housing 16 will result when penetrating a thrombus. Also less force will be required by the physician at the point of percutaneous entry. Using a representative drive shaft 14 having diameter of 0.2 mm (corresponding to 0.008" or 8 mils) the RPM required to have a circumferential component of velocity equal to a typical longitudinal advance velocity of 10 mm per second is:

$$RPM = \frac{10 \text{ mm/sec}}{(.2 \text{ mm})(\pi)} \times 60 \text{ sec/min} = 955 \text{ RPM}$$

Assuming isotropic coefficients of friction for orthogonal directions of slip, this implies a longitudinal friction force equal to a circumferential friction force or a reduction of longitudinal friction by about 30%. In this same example, the fibrin forms a helix around the drive shaft with a pitch of one part in one or 45°. This implies engagement of a large amount of fibrin network per single rotation and hence an increase in the amount of torque required to break the fibrin fibers away from their radially more distant neighbors. Operation at 4000 RPM has been shown to reduce total torque required to a low level for a typical advance rate of approximately 10 mm per second and to provide a good target RPM for general applications. At 4000 RPM, the orthogonal displacement of longitudinal friction is more than 75% in the above example, thus reducing force required in the longitudinal direction to less than 25% of its non-rotating level. Of course, parts of the system with larger radii of gyration will experience an even larger reduction in the amount of longitudinal force required vis-a-vis the non-rotating case.

The device 10 is generally operated in one of two different modes. In the first mode, the shaft housing 16 with the tip 12 withdrawn into it is advanced to the thrombus. The rotating tip 12 is then advanced out of the shaft housing 16 by advancing the drive shaft 14 axially through the seal 30.

In the second mode of operation, the tip 12 and shaft housing 16 are advanced collectively with the tip 12 held a distance of about 5 mm in front of the shaft housing 16.

Figure 5:
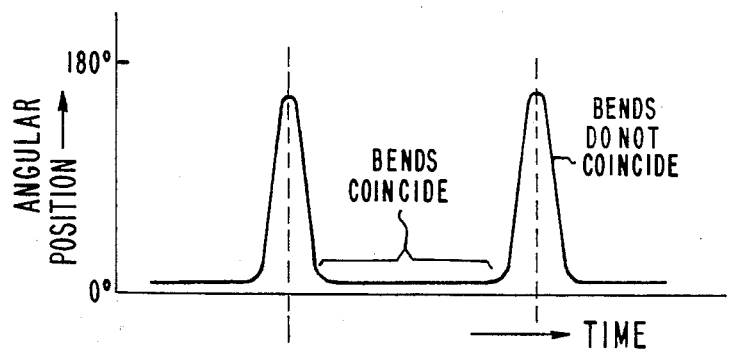
FIG. 5 is a graph illustrating the proportion of time the bends of the shaft housing and the drive shaft coincide in the embodiment of FIG. 4.

FIG. 4 depicts a steerable embodiment 200 of the present invention. Steerability is accomplished by preforming the distal segment of the shaft housing 216 to have a gentle arched region 215 as shown. Rotation of the entire shaft housing 216 by the angiographer points the distal segment of the shaft housing 216 in a given off-axis direction. Such steerability may be coupled with a drive shaft 214 which is straight or preformed to have its arch (not shown) potentially overlapping that of the shaft housing 216. When such overlap occurs, the system 200 resists rotation of the drive shaft 214 since the two bends are in synchrony with each other. When the system 200 is forced to rotate, the relative time spent with an angular orientation such that the bends coincide is greater than that spent when they are in opposition. FIG. 5 provides a qualitative picture of the proportional time spent as the system is rotationally driven. The angiographer may steer the system into a desired branch vessel by rotating the shaft housing 216 to point in the direction of the desired branch. A swivel connector 218 facilitates rotation of the shaft housing 216. Since the system 200 spends more time in the angular position with preformed arches overlapping, the tip 212 will have an enhanced probability for entering the desired branch vessel as it is advanced, provided the steering is correct.

While the device 10 has been described for use in coronary thrombectomies, other uses, such as the endoscopic removal of clots from the stomach or other cavities via transmission through the operating channel of the endoscope and the removal of other abnormal intracorporeal fibrous mass or fiber reinforced mass, are additional applications for the device.

I claim:

1. A transluminal thrombectomy apparatus comprising:
   (a) a flexible drive shaft having a tip affixed to the distal end thereof, said tip being solid and having a proximal end and a distal end, the ends of said tip being rounded, and the entire exterior surface of said tip being continous and smooth, whereby said tip is not capable of cutting or of injuring the wall of a lumen;
   (b) a flexible, cylindrical shaft housing, said flexible drive shaft extending through said shaft housing and through shaft housing connecting means at its proximal end, said shaft housing connecting means connecting said shaft housing to a drive shaft bearing block and seal, whereby a fluid path will exist from said shaft bearing block down through said shaft housing;
   (c) a rotating prime mover; and
   (d) drive shaft connecting means at the proximal end of said drive shaft which extends through said shaft housing connecting means for connecting said drive shaft to said rotating prime mover.

2. The transluminal thrombectomy apparatus of claim 1 wherein said flexible drive shaft is comprised of a flexible, solid shaft.

3. The transluminal thrombectomy apparatus of claim 2 wherein said shaft is made of a radiopaque material.

4. The transluminal thrombectomy apparatus of claim 3 in which said shaft is made of stainless steel.

5. The transluminal thrombectomy apparatus of claim 3 wherein said helical metal winding is comprised of a radiopaque material.

6. The transluminal thrombectomy apparatus of claim 5 wherein said helical metal winding is bonded to said solid shaft.

7. The transluminal thrombectomy apparatus of claim 6 wherein the metal of said helical metal winding is selected from the group consisting of gold and platinum.

8. The transluminal thrombectomy apparatus of claim 2 wherein said flexible drive shaft further comprises a helical metal winding over said solid shaft.

9. The transluminal thrombectomy apparatus of claim 1 wherein said tip is an elongated cylinder with rounded shoulders adjacent to and remote from said shaft housing.

10. The transluminal thrombectomy apparatus of claim 9 wherein said tip is formed from radiopaque substance.

11. The transluminal thrombectomy apparatus of claim 1 wherein said tip is spheroidal in shape.

12. The transluminal thrombectomy apparatus of claim 11 wherein said tip is formed from radiopaque substance.

13. The transluminal thrombectomy apparatus of claim 1 wherein said flexible, cylindrical shaft housing is comprised of a cylindrical plastic tube having a fluid connector at its end which is remote from said tip.

14. The transluminal thrombectomy apparatus of claim 13 wherein said fluid connector connects to an apparatus capable of providing a fluid path through said shaft housing to the end of said shaft housing at which said tip is located, and said apparatus also includes a seal means through which said drive shaft extends, said seal means being adapted to permit axial movement of said drive shaft therethrough while said transluminal thrombectomy apparatus is in use.

15. The transluminal thrombectomy apparatus of claim 1 wherein said shaft housing includes a formed bend therein adjacent to the end of said shaft housing from which said tip extends, whereby steerability through alternative selection of vessels can be accomplished.

16. The transluminal thrombectomy apparatus of claim 1 wherein the inside diameter of said flexible, cylindrical shaft housing is greater than the outside diameter of said tip, said shaft housing extending along and surrounding said drive shaft.

17. The transluminal thrombectomy apparatus of claim 1 further comprising connecting means for sealably connecting the end of said shaft housing which is remote from said tip to an apparatus capable of providing a fluid path through said shaft housing to the end of said shaft housing at which said tip is located.

18. The transluminal thrombectomy apparatus of claim 1 wherein said tip has a diameter which is greater than that of said drive shaft.

* * * * *